(12) United States Patent
Wilson et al.

(10) Patent No.: US 8,879,274 B2
(45) Date of Patent: Nov. 4, 2014

(54) METHOD OF MANUFACTURING AN ELECTRICAL COMPONENT

(75) Inventors: Alan Wilson, Glen Iris (AU); Peter Vincent, Ivanhoe (AU); Richard Muscat, Moonee Ponds (AU)

(73) Assignee: The Commonwealth of Australia—Department of Defence, Canberra (AU)

( * ) Notice: Subject to any disclaimer, the term of this patent is extended or adjusted under 35 U.S.C. 154(b) by 1608 days.

(21) Appl. No.: 10/581,552

(22) PCT Filed: Dec. 1, 2004

(86) PCT No.: PCT/AU2004/001686
§ 371 (c)(1),
(2), (4) Date: Mar. 20, 2007

(87) PCT Pub. No.: WO2005/055680
PCT Pub. Date: Jun. 16, 2005

(65) Prior Publication Data
US 2007/0173048 A1     Jul. 26, 2007

(30) Foreign Application Priority Data
Dec. 5, 2003 (AU) ............................... 2003906776

(51) Int. Cl.
*H05K 7/00* (2006.01)
*C23F 4/00* (2006.01)
*G01N 17/04* (2006.01)
*H05K 3/02* (2006.01)
*H05K 1/16* (2006.01)
*H05K 3/00* (2006.01)

(52) U.S. Cl.
CPC *C23F 4/00* (2013.01); *G01N 17/04* (2013.01); *H05K 3/027* (2013.01); *H05K 1/162* (2013.01); *H05K 1/165* (2013.01); *H05K 3/0038* (2013.01); *H05K 2201/0187* (2013.01); *H05K 2201/10151* (2013.01)
USPC ........... 361/760; 361/728; 361/736; 361/742; 174/250; 174/257; 174/261

(58) Field of Classification Search
USPC .......... 361/760, 728, 736, 742; 174/250, 257, 174/261, 262
See application file for complete search history.

(56) References Cited

U.S. PATENT DOCUMENTS 5,095,278 A    3/1992 Hendrick
5,313,836 A *  5/1994 Fujii et al. .................. 73/514.16
(Continued)

FOREIGN PATENT DOCUMENTS

DE    1690542 A1    11/1971
DE    3245272 A1    6/1984
(Continued)

OTHER PUBLICATIONS

Kickelhain, Jörg, "Mikrostrukturierung mittels Lasertechnik," Jan. 1, 1990, pp. 38-40, No. ¾, SMD-Magazin.

*Primary Examiner* — Andargie M Aychillhum
(74) *Attorney, Agent, or Firm* — Douglas E. Jackson; Stites & Harbison PLLC

(57) ABSTRACT

There is disclosed a method of manufacturing an electrical component, involving bonding a thin metal foil to an insulating substrate and thereby forming a component blank, and laser machining at least the metal foil of said component blank to produce at least one trench for defining one or more foil tracks, said trench being at least equal in depth to the thickness of the foil so as to prevent current flow across the trench.

39 Claims, 2 Drawing Sheets

(56) References Cited

U.S. PATENT DOCUMENTS

| | | | |
|---|---|---|---|
| 5,493,076 A * | 2/1996 | Levite et al. | 174/261 |
| 6,349,038 B1 * | 2/2002 | Hailey | 361/794 |
| 6,513,362 B1 * | 2/2003 | Yadav et al. | 73/31.05 |
| 2004/0025333 A1 * | 2/2004 | Hirose et al. | 29/830 |
| 2004/0089471 A1 * | 5/2004 | Andoh et al. | 174/262 |
| 2005/0116718 A1 * | 6/2005 | Chen et al. | 324/338 |

FOREIGN PATENT DOCUMENTS

| | | |
|---|---|---|
| DE | 3431446 A1 | 3/1986 |
| GB | 811295 | 4/1959 |
| JP | 11121904 | 4/1999 |

* cited by examiner

METHOD OF MANUFACTURING AN ELECTRICAL COMPONENT

FIELD OF THE INVENTION

The present invention relates to a method of manufacturing an electrical component, and to electrical components manufactured by that method. The method is suited to manufacturing foil sensors. Such foil sensors are of particular but by no means exclusive suitability as corrosion sensors for monitoring corrosion in inaccessible locations or under protective surfaces, and for monitoring the structural health of high value structures.

BACKGROUND OF THE INVENTION

Foil sensors are composed of a thin metal foil bonded to an insulating substrate, and are used in monitoring the structural health of high value structures.

However, existing sensors are manufactured by techniques that in each case are suitable for only a small range of foil materials. Consequently, such foils are not generally made of the parent structural material to be monitored; the corrosion detected by the sensor must therefore be related by some means to the corrosion on the parent structure. This may be described as an indirect monitoring approach; it can produce errors and it restricts the use of existing sensors to structures where the sensor/structure relationship is known.

Further, existing small structure manufacturing techniques used in the manufacture of sensors means that only a limited number of materials can be used in sensor manufacture, so the breadth of existing sensor types is small. These existing techniques also have difficulty producing thin foils and adhering thin foils to rigid insulating backings.

SUMMARY OF THE INVENTION

According to the present invention, there is provided a method of manufacturing an electrical component, involving:
bonding a thin metal foil to an insulating substrate and thereby forming a component blank; and
laser machining at least the metal foil of said component blank to produce at least one trench for defining one or more foil tracks, said trench being at least equal in depth to the thickness of the foil so as to prevent current flow across the trench.

The method preferably includes filling said trench with an insulating material.

Preferably the insulating material is a polymer.

Preferably said polymer comprises an epoxy resin, such as EPOTHIN™ brand epoxy resin.

The method preferably includes forming said metal foil from a parent foil that is substantially identical with the material of the structure to be monitored.

The method may also include laser machining said component blank to produce one or more back slots, said slots being equal in depth to the full thickness of said sensor. The back slots can then be used for the purpose of filling the trenches with a trench filling material, e.g. an insulating material.

The method preferably includes preparing the metal foil by machining a sample of parent material to a desired final thickness. More preferably the method includes alternately machining both faces of the parent material until said final thickness is achieved.

Machining in this manner removes any surface finish due to processes such as rolling, plating or heat treating, produces a relatively stress free material, and thins the parent material without effecting the material properties (unlike thinning by chemical milling or rolling). Milling may be performed from one surface only if it is desired to maintain a completely pristine surface as the sensing surface. A light chemical etch with the sensing surface protected can be performed on the milled surface to remove any stresses introduced by the milling process.

Preferably the method includes preparing the foil for said bonding by applying a chemically resistant film (such as a polyester tape) to a first face of said foil, and dipping the other face of said foil in a bond enhancer (such as a 1% silane solution), wherein said first face is ultimately the exposed face and said chemically resistant film protects said first face from said bond enhancer.

Preferably the method includes drying said foil and then removing said film.

Preferably the substrate has an ablation rate that is sufficiently low to prevent unwanted penetration of the substrate during machining to remove said foil.

Preferably said substrate comprises a plurality of layers of fibreglass prepreg.

Preferably where the electrical component is a metal foil sensor the method includes preparing said component blank by coating said component blank on the surface comprising the ultimate sensor side of said sensor with a chemically resistant coating solution, to protect said surface from contamination during sensor processing. More preferably the method includes then drying said sensor blank.

Preferably said laser machining said foil comprises producing slots, in one embodiment of approximately 150 μm length at 1.5 mm intervals. Preferably a polymer is introduced into the trenches preferably using the slots.

The invention also provides an electrical component produced according to the above method.

The invention still further provides an electrical component, comprising:
an insulating substrate;
a thin metal foil bonded to said insulating substrate; and
at least one laser machined trench for defining one or more foil tracks so as to prevent current flow across the trench, said trench being at least equal in depth to the thickness of the foil.

Electrical components that can be made using this method include, for example, linear polarisation resistance gauges, electrochemical impedance spectrometry gauges, corrosion resistance gauges, spiral inductors and delay circuits.

BRIEF DESCRIPTION OF THE DRAWINGS

In order that the invention may be more clearly ascertained, an embodiment will now be described, by way of example, with reference to the accompanying drawings, in which.

DETAILED DESCRIPTION

Figure 1:
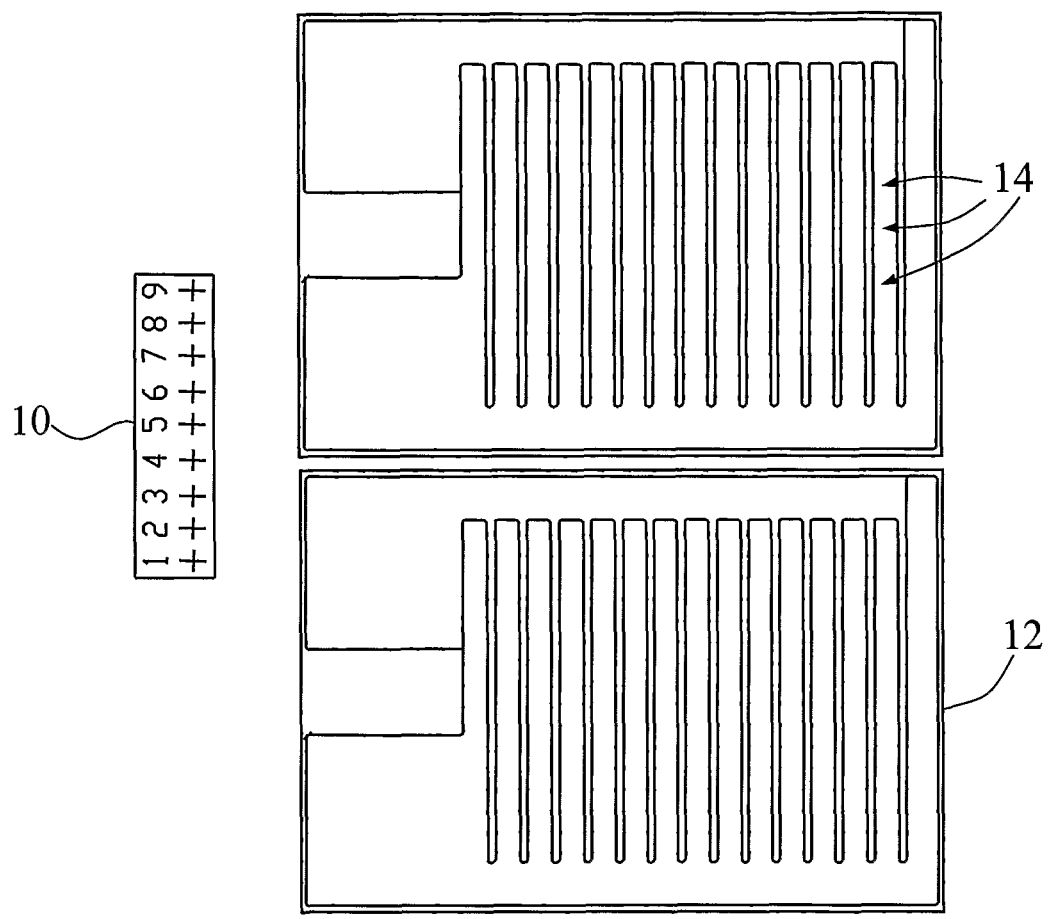
FIG. 1 is a diagram of the three laser path files used in the laser machining of a pair of sensors according to an embodiment of the present invention.

According to one embodiment of the present invention, foil sensors were manufactured by the following method, described by reference to the exemplary manufacture of an aluminium foil sensor.

Firstly, a thick parent foil material (in this embodiment, aluminium) was machined by alternately machining both faces of the parent material until a final thickness of 80 µm was achieved. During the machining, a fine pitch vacuum chuck was used to hold the material down, and thermal and stability effects were minimized by using a large milling machine. The vacuum chuck was machined 'true' before commencing the process.

Machining in this manner removes any surface finish due to processes such as rolling, plating or heat treating, produces a relatively stress free material, and thins the parent material without effecting the material properties.

The foil was then prepared for bonding. The foil was degreased and cleaned: in order not to change the surface properties of the foil, it was subjected to the following:

An acetone wash;
A distilled water wash;
A 30% nitric acid wash;
A distilled water wash;
Light wet abrasion of the non-sensor face with 800 grit paper;
A distilled water wash;
Nitrogen drying; and
Baking for 1 h at 110°C.

A chemically resistant adhesive polyester tape was then applied to one face of the foil (i.e. the face ultimately to become the exposed face of the sensor) to protect it from the bond enhancer. A suitable tape, ECONOBREAKER™ brand tape supplied by Airtech International, Inc., was used for this purpose.

The other face was then dip coated for 15 min with a bond enhancer comprising a 1% silane solution (which had been mixed for 30 min before use).

The sample was oven dried at 45° C. for 1 h, after which the tape was removed.

The foil was then bonded to the substrate. The prepreg used for the substrate, comprising 0.003 inch (76 µm) FR4 Fibreglass prepreg, was prepared by drying the prepreg in a vacuum oven at 40° C. and 2 kPa for 24 h. This material was chosen as its ablation route is sufficiently low to prevent unwanted penetration during machining, for example when an additional pass of the laser is required to remove remnants of foil.

The prepared foil was bonded to three layers of prepreg in a bonding press under 3 kN over 150 mm$^2$, at 175° C. for 1 h. The resulting sensor material was cut into 25×75 mm sensor blanks ready for laser machining. However, it will be appreciated that sensors can be manufactured in large strips.

A thin chemically resistant coating solution was prepared, so that the sensor blanks could be coated on the sensor side to protect that surface from contamination during sensor processing. This was done by attaching the sensor blank with double sided tape to a flat glass carrier and positioning the blank/slide centrally on a stationary spin coater. A thick layer of the coating solution was applied and, using a gloved finger, the solution was gently and evenly spread over the surface until an even coat of ~1 mm thickness was produced. The spinner was spun up to 3900 rpm for 10 s to produce a thin even coat of protective film.

Those skilled in the art will appreciate that there are a number of manual and automatic techniques for applying protective coatings. For instance a spray could be used to apply the protective coating and this would be particularly useful for processing long strips of material.

In this example the coating solution comprised a mixture of 50% LACOMIT™ brand vinyl based coating solution and 50% LACOMIT™ brand thinner, both by Agar Scientific Limited. Other comparable coating materials that might prove suitable include Crystalbond 509™ brand mounting adhesive and Microshield™ brand protectant, both by Structure Probe, Inc.

The blanks were dried in a 35° C. oven for 4 hours.

The sensor blanks were laser machined to form trenches in the blanks as follows.

The sensor blank/slide were positioned, using a locating jig, under the laser cutter. Three laser path files were used in the machining:
1) Setup file;
2) Sensor Cutting file; and
3) Sensor Backfile Slotting file.

The blank was translated in the x direction and another pair of sensors was then machined. This continued along the length of the sensor material.

Figure 2A:
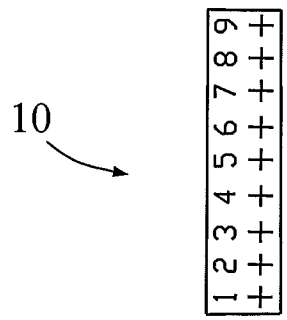
FIG. 2A is a further diagram of the setup file pattern of FIG. 1.
Figure 2B:
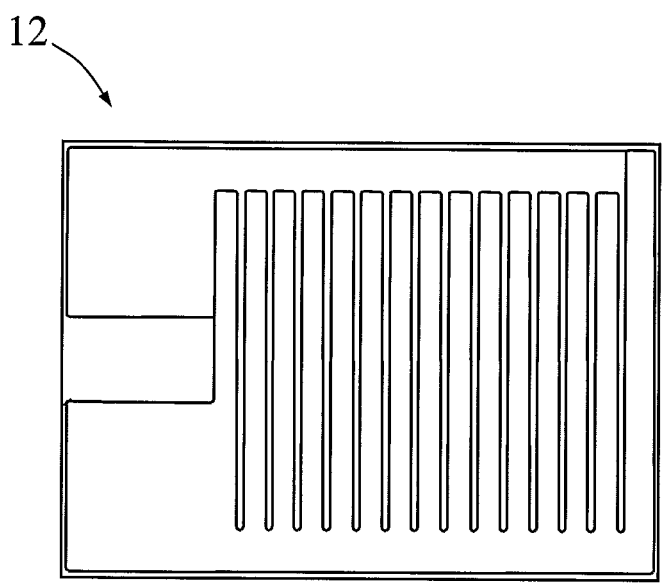
FIG. 2B is a further diagram of the sensor cutting file pattern of FIG. 1.
Figure 2C:
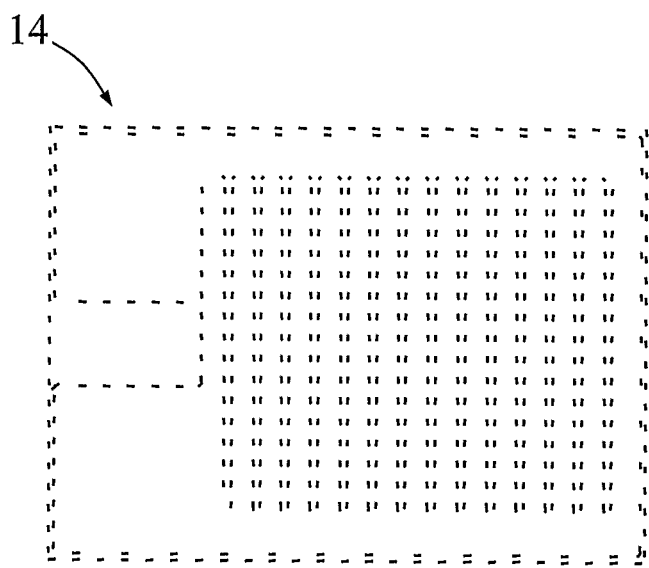
FIG. 2C is a further diagram of the sensor back slotting file pattern of FIG. 1.

FIG. 1 is a diagram of the patterns produced by the three laser path files employed in the laser machining of the sensor blank and pair of sensors thereon. This includes the setup file pattern 10, the sensor cutting file pattern 12, and the sensor backfile slotting file pattern 14. For clarity, each pattern is also shown separately in FIG. 2A (the setup file pattern 10), FIG. 2B (the sensor cutting file pattern 12 for a single sensor) and FIG. 2C (the sensor backfile slotting file pattern 14 for a single sensor). In the example shown, the patterns are for machining a pair of twin electrode sensors, for use—for example—as linear polarization resistance gauges or an electrochemical impedance spectrometry gauges.

The Setup File: this file produces multiple scans over a non-sensor area of the blank material. From post inspection it was possible to gauge the number of laser scans necessary to cut through the aluminium foil and the fibreglass (as required when cutting slots in the sensor), and the number of scans necessary to cut through the aluminium foil completely but leave the fibreglass essentially intact (as required when cutting the sensor pattern out).

The Sensor Cutting file: this file is used to cut the trenches that define the sensor pattern. The number of laser scans is set according to the results of the setup process, that is, the correct number of scans to penetrate the foil but not the fibreglass substrate.

The Slotting file: this file puts 150 µm back slots at 1.5 mm intervals along the sensor pattern. The number of scans is set to fully penetrate the foil and the fibreglass substrate.

It will be appreciated by the skilled person that, during laser machining, ablation products form on the sensor face close to the trench edge. These were removed by subjecting the sensors to the following:

Ultrasonic cleaning for 2 min in a 20% NaOH solution;
Immersion in 70% nitric acid until reaction (evidenced by bubbling) stops;
A distilled water wash; and
Nitrogen drying.

The protective film of LACOMIT™ brand coating solution protects the bulk of the surface from chemical attack during this removal of ablation products.

The protective film covering the sensor was then removed with a suitable solvent, LACOMIT™ brand Remover by Agar Scientific Limited, a xylene based product selected so as not to effect the sensor surface.

Trench filling was conducted as follows. A high temperature polyester adhesive tape was applied to the sensor face. FLASHBREAKER 2R™ brand tape by Airtech International, Inc. was selected for this purpose, as high temperature tape has fewer volatile substances so does not outgas to as great extent as some alternatives.

The sensor was taped along its edge, fibreglass side up, to the base of a shallow container and dried in a vacuum oven for 12 h at 60° C. at 2 kPa.

The oven was vented and a low viscosity epoxy resin (in this example, EPOTHIN™ brand epoxy resin by Buehler Ltd) was introduced from a container above the sensor. (This container had a drain plug that can be operated from outside the chamber.) The vacuum was re-established and the epoxy allowed to outgas for a few minutes.

Care was exercised in the outgassing of the epoxy resin; the vacuum was hard enough to remove air introduced during the epoxy mixing, but not so hard as to 'boil' the low density components out of the epoxy. Also, outgassing was kept brief (between 10 to 15 min) so that the epoxy did not start to cure.

While still under vacuum and using remote control, the resin was allowed to flow into the sensor, that is, the sensor was essentially immersed in the resin.

The oven was vented, to force the resin to flow through the back slots and into the trenches. Filling the trenches through the back slots allows it to be introduced without contaminating the sensing surface.

In the final assembly stage, the sensors were removed from the resin and excess resin was removed. The sensors were then cured in an oven at 50° C. for 24 h.

The protective tape was removed, and the surface cleaned with turpentine to remove any residual adhesive, washed with ethanol, rinsed in distilled water and dried with nitrogen.

Finally, the completed foil sensors were separated into individual elements either by guillotining or by snapping the sensor off along the lines of the outer machined rectangle. If the slots are machined to enable the snapping off, the machining should weaken the underlying substrate sufficiently for this to be a reliable separation technique.

Foil sensors manufactured according to the above embodiment of the present invention can advantageously be formed of the same material as that which they are intended to monitor; the ability to use material that is the same as the monitored structure simplifies the correlation of sensor results with what is occurring on the structure. For example, corrosion activity on an aluminium alloy structure can be correlated with a corrosion sensor made of precisely the same material.

Such foils sensors can be made with fine feature size. The ability to machine stable structures in the tens of microns range enables electrical parameters to be scaled to a point where they can be reliably measured.

Methods such as described above are suitable for manufacturing electronic components where the thin metal foil is in the range of 15 to 200 μm in thickness, although. It will be appreciated that thicker metal foils could be used but as a result the cutting process becomes more difficult and higher power lasers may be required. The typical minimum spacing between the electrodes (i.e. metal tracks) is the cutting width of the laser beam which in this example is 25 to 30 μm. This closer separation of electrodes (i.e. the trench width) allows sensors of higher sensitivity to be produced. Although, it will be appreciated that depending on the application wider trenches may be suitable, for example to adjust the sensitivity of a device.

Metal foil sensors produced according to the method have a closer spacing of elements in the sensors because they are produced using laser machining rather than a chemical etching process. Further, this allows sensor fabrication to be largely independent of the metal that the sensor is being fabricated in unlike a chemical process. Resistance sensors of superior sensitivity due to the higher resistance obtained using long, thin, compact serpentine patterns can be produced. Further, flat inductive devices and sensors will have a lower resistance and higher inductance than similar sized devices produced using etching process.

The ratio of depth of the trench to width of the trench can be in the range of 1:1 to 7:1 while maintaining substantially straight trench walls. This compares with typical etching processes which are only capable of producing ratios of about 1:1 and also have a much larger amount of undercut—i.e. the walls will be angled. The relative lack of undercut allows:

the production of better spirals;
the production of thinner slots;
effective backfilling; and
easier sensing of changes in any dielectric trench filling material.

Further, such thin metal sensors are more robust than their counterpart sensors formed from vapour deposition where the layer of metal may only be a micron thick. This allows them to be used in environments requiring a more robust sensor—e.g. corrosion sensors.

Multiple types of corrosion sensor can be manufactured using the process, including corrosion sensors (whether electrochemical or resistance (labyrinth) sensors), fatigue gauges and continuity gauges. Further, two or more different types of sensors can be incorporated as part of the same foil sensor—e.g. a resistance sensor and a corrosion sensor. These sensors can also be situated under paint and sealant beads The thin sensors manufactured in accordance with embodiments of the invention make them ideal for applications under paints or sealants or other narrow locations to monitor the integrity of the paint or sealant or whether corrosion is occurring in the narrow location.

Persons skilled in the art will appreciate that other electrical components that can be made of foil tracks can be manufactured using methods as exemplified above. For example, spiral inductors are useful in flat radio frequency circuits and also in flat eddy current non-destructive testing sensors and can be produced using the above method. The advantage of the above technique for spiral inductors is that spirals are produced with straight edges to give higher density, and lower resistance for achieved inductance than chemical etching processes. Capacitors can also be produced.

Furthermore, the material is preferably milled to size, rather than rolled or chemically etched to size. Milling allows the material to retain important properties, whereas these other two methods alter such properties.

In embodiments where the method involves filling of the trenches with an insulator, this plays the important role of protecting the edges of the metal so that corrosion only occurs at the face of the sensor. This is important to maintain the same corrosion characteristics as the structure being monitored and is especially important for aluminium alloys in which edge corrosion known as exfoliation occurs very rapidly compared to face corrosion. For example, by preventing water from getting between the foil tracks. However, when components have other applications such as spiral inductors for a radio circuit, an insulating material will not be needed as the metal tracks are electrically isolated by the air gap between tracks and the insulating substrate. Persons skilled in the art will also appreciate that while a polymer insulating material will typically be used, other insulating materials can be used.

The trench filling material can also be an active part of the sensor such as a dielectric that changes its properties on exposure to certain agents. The change in the dielectric properties is then detected by a change in the electrical response of the sensor electrodes.

The trench filling material can also enhance the properties of the sensor. For example a material bearing particles with magnetic properties could be used to modify the properties of spiral inductors.

Modifications within the scope of the invention may be readily effected by those skilled in the art, for example to convert the above method into a method more suited for mass production. It is to be understood, therefore, that this invention is not limited to the particular embodiments described by way of example hereinabove.

Any reference herein to prior art is not intended to imply that such prior art forms or formed a part of the common general knowledge.

The invention claimed is:

1. A method of manufacturing an electrical sensor with an exposed sensing surface, comprising the steps of:
    bonding an integral thin metal foil to an insulating substrate and thereby forming a component blank having an outer metal face of said metal foil;
    laser machining the outer metal face of the metal foil bonded to the insulating substrate of said component blank to produce at least one trench which defines one or more foil tracks cut through the metal foil of the component blank, said laser machining including the steps of
    a) preventing penetration of the insulating substrate, and
    b) forming said at least one trench to be at least equal in depth to the thickness of the thin metal foil to prevent current flow across the at least one trench between the one or more foil tracks;
    laser machining the insulating substrate of said component blank to produce one or more back slots in the insulating substrate connected to the at least one trench, whereby said one or more back slots and said at least one trench are together equal in depth to the full thickness of said component blank; and
    filling said at least one trench with a trench filling material;
    wherein said electrical sensor comprises said component blank, or is manufactured from said component blank, once said at least one trench has been filled with said trench filling material, and
    wherein said electrical sensor has an exposed sensing surface comprising said outer metal face of said metal foil.

2. A method as claimed in claim 1, including performing said laser machining by a laser with a cutting width, and creating the one or more foil tracks with a spacing approximately equal to said cutting width.

3. A method as claimed in claim 1, wherein said cutting width is from 25 to 30 μm.

4. A method as claimed in claim 1, wherein said trench filling material is an insulating material.

5. A method as claimed in claim 4, wherein said insulating material is one of an epoxy resin or other polymer.

6. A method as claimed in claim 1, wherein said trench filling material is a dielectric material and said electrical sensor responds to changes in said dielectric material.

7. A method as claimed in claim 1, wherein said electrical sensor is a foil sensor, and said method further comprises forming said metal foil from a parent foil that is substantially identical with the material of a structure to be monitored.

8. A method as claimed in claim 1, wherein said laser machining of said insulating substrate of said component blank produces said one or more back slots to be of approximately 150 μm length at 1.5 mm intervals.

9. A method as claimed in claim 1, wherein said step of filling said at least one trench includes introducing the trench filling material into said at least one trench via said one or more back slots.

10. A method as claimed in claim 1, further comprising preparing the metal foil by machining a sample of parent material to a desired final thickness.

11. A method as claimed in claim 10, comprising alternately machining both faces of the parent material until said final thickness is achieved.

12. A method as claimed in claim 1, further comprising preparing the metal foil for said bonding by applying a chemically resistant film to the outer metal face of said metal foil, and applying a bond enhancer to the other face of said metal foil, wherein said outer metal face is ultimately the exposed sensing surface and said chemically resistant film protects said outer metal face from said bond enhancer.

13. A method as claimed in claim 12, comprising drying said foil and then removing said film.

14. A method as claimed in claim 12, wherein said chemically resistant film comprises a polyester tape.

15. A method as claimed in claim 1, wherein the material of said insulating substrate is chosen to have an ablation rate that is sufficiently low to prevent unwanted penetration of the substrate during said laser machining step.

16. A method as claimed in claim 15, wherein said insulating substrate comprises a plurality of layers of fibreglass prepreg.

17. A method as claimed in claim 1, wherein said electrical sensor is a foil sensor and the method further comprises preparing said component blank by coating said component blank on the outer metal face comprising the ultimate exposed sensor surface of said component blank with a chemically resistant coating solution, to protect said outer metal face from contamination during sensor processing.

18. A method as claimed in claim 17, comprising drying said component blank after coating said component blank.

19. A method as claimed in claim 1, comprising laser machining said component blank to form two different types of sensors.

20. A method as claimed in claim 1, wherein said electrical sensor is selected from the group consisting of:
    a linear polarisation resistance gauge;
    a corrosion sensor;
    a resistance sensor;
    a non-destructive testing sensor;
    a spiral inductor;
    a delay line sensor;
    a capacitive sensor; and
    a sensor responsive to changes in a dielectric material.

21. A method as claimed in claim 1, including producing said at least one trench with a ratio of depth to width of from 1:1 to 7:1.

22. A method as claimed in claim 1, including forming said at least one trench with side walls that are substantially straight.

23. An electrical sensor produced according to the method of claim 1.

24. A foil sensor produced according to the method of claim 1.

25. An electrical sensor with an exposed sensing surface, comprising:
    an insulating substrate;
    a thin metal foil that has been bonded while integral to said insulating substrate;
    an outer metal face of said thin metal foil;
    at least one trench in the thin metal foil which defines one or more foil tracks in the thin metal foil so as to prevent current flow across the at least one trench, said at least one trench a) being formed by laser machining of the outer metal face of the thin metal foil bonded to the insulating substrate while preventing the at least one trench from penetrating the insulating substrate, and b) being at least equal in depth to the thickness of the foil;

one or more back slots in the insulating substrate and connected to the at least one trench, said one or more back slots and said at least one trench are together equal in depth to the combined thickness of said thin metal foil and said insulating substrate; and a trench filling material which fills said at least one trench, but which leaves an exposed sensing surface comprising said outer metal face of said thin metal foil.

26. An electrical sensor as claimed in claim 25, wherein said at least one trench is laser machined by a laser with a cutting width, and said one or more foil tracks have a spacing between adjacent pairs of the foil tracks that is approximately equal to said cutting width.

27. An electrical sensor as claimed in claim 25, wherein said cutting width is from 25 to 30 µm.

28. An electrical sensor as claimed in claim 25, wherein said trench filling material is an insulating material.

29. An electrical sensor as claimed in claim 28, wherein said insulating material is one of an epoxy resin or other polymer.

30. An electrical sensor as claimed in claim 25 wherein said trench filling material is a dielectric material.

31. An electrical sensor as claimed in claim 25, wherein said electrical sensor comprises at least one of:

a linear polarisation resistance gauge;
a corrosion sensor;
a resistance sensor;
a non-destructive testing sensor;
a spiral inductor;
a delay line sensor;
a capacitive sensor; and
a sensor responsive to changes in a dielectric material.

32. An electrical sensor as claimed in claim 25, wherein said electrical sensor comprises two or more different types of foil sensors.

33. An electrical sensor as claimed in claim 25, wherein the thin metal foil has a thickness in the range of 15 to 200 µm.

34. An electrical sensor as claimed in claim 25, wherein said at least one trench has a ratio of depth to width of from 1:1 to 7:1.

35. An electrical sensor as claimed in claim 25, wherein said at least one trench has side walls that are substantially straight.

36. An electrical sensor as claimed in claim 25, wherein said insulating substrate is formed of a material having a sufficiently low rate of ablation to prevent unwanted penetration of the substrate during said laser machining.

37. An electrical sensor as claimed in claim 36, wherein said substrate comprises a plurality of layers of fibreglass prepreg.

38. An electrical sensor as claimed in claim 25, wherein said electrical sensor is a foil sensor and said thin metal foil is from a parent foil that is substantially identical with the material of a structure to be monitored.

39. An electrical sensor as claimed in claim 25, wherein said one or more back slots are approximately 150 µm length at 1.5 mm intervals.

* * * * *